United States Patent
Chen et al.

(10) Patent No.: US 12,251,081 B2
(45) Date of Patent: *Mar. 18, 2025

(54) ENDOSCOPE TIP ASSEMBLY USING TRUNCATED TRAPEZOID CAVITY INTERPOSER TO ALLOW COPLANAR CAMERA AND LEDS IN SMALL-DIAMETER ENDOSCOPES

(71) Applicant: OmniVision Technologies, Inc., Santa Clara, CA (US)

(72) Inventors: Teng-Sheng Chen, Hsinchu (TW); Wei-Ping Chen, New Taipei (TW); Wei-Feng Lin, Hsinchu (TW); Jau-Jan Deng, Taipei (TW)

(73) Assignee: OmniVision Technologies, Inc., Santa Clara, CA (US)

( * ) Notice: Subject to any disclaimer, the term of this patent is extended or adjusted under 35 U.S.C. 154(b) by 430 days.

This patent is subject to a terminal disclaimer.

(21) Appl. No.: 17/747,803

(22) Filed: May 18, 2022

(65) Prior Publication Data
US 2023/0118866 A1    Apr. 20, 2023

Related U.S. Application Data

(63) Continuation-in-part of application No. 17/504,105, filed on Oct. 18, 2021, now Pat. No. 12,064,090.

(51) Int. Cl.
*A61B 1/00* (2006.01)
*A61B 1/05* (2006.01)
*A61B 1/06* (2006.01)

(52) U.S. Cl.
CPC .......... *A61B 1/051* (2013.01); *A61B 1/00096* (2013.01); *A61B 1/0638* (2013.01); *A61B 1/0684* (2013.01)

(58) Field of Classification Search
CPC ... A61B 1/051; A61B 1/00096; A61B 1/0638; A61B 1/0684
See application file for complete search history.

(56) References Cited

U.S. PATENT DOCUMENTS 9,538,909 B2   1/2017 Lei et al.
9,913,573 B2   3/2018 Banik et al.
(Continued)

FOREIGN PATENT DOCUMENTS

EP    1839559 B1    9/2015
EP    2687144 B1    11/2017
WO    WO 2018/136950 A1    7/2018

OTHER PUBLICATIONS

U.S. Appl. No. 17/674,675 Office Action dated Mar. 2, 2023, 20 pages.
(Continued)

*Primary Examiner* — Timothy J Neal
(74) *Attorney, Agent, or Firm* — COZEN O'CONNOR

(57) ABSTRACT

A cavity interposer has a cavity, first bondpads adapted to couple to a chip-type camera cube disposed within a base of the cavity at a first level, the first bondpads coupled through feedthroughs to second bondpads at a base of the interposer at a second level; and third bondpads adapted to couple to a light-emitting diode (LED), the third bondpads at a third level. The third bondpads coupled to fourth bondpads at the base of the interposer at the second level; and the second and fourth bondpads couple to conductors of a cable with the first, second, and third level different. An endoscope optical includes the cavity interposer an LED, and a chip-type camera cube electrically bonded to the first bondpads; the LED is bonded to the third bondpads; and a top of the chip-type camera cube and a top of the LED are at a same level.

16 Claims, 5 Drawing Sheets

(56) References Cited

U.S. PATENT DOCUMENTS

| | | |
|---|---|---|
| 11,147,437 B1 | 10/2021 | Ochi et al. |
| 11,172,806 B2 * | 11/2021 | Chen et al. |
| 12,064,090 B2 * | 8/2024 | Chen .................. A61B 1/00096 |
| 2003/0220574 A1 | 11/2003 | Markus et al. |
| 2004/0038447 A1 | 2/2004 | Corisis |
| 2005/0143623 A1 | 6/2005 | Kojima |
| 2005/0174473 A1 | 8/2005 | Morgan et al. |
| 2005/0236708 A1 | 10/2005 | Farnworth et al. |
| 2005/0267328 A1 | 12/2005 | Blumzvig et al. |
| 2005/0275748 A1 | 12/2005 | Takekuma et al. |
| 2007/0206114 A1 | 9/2007 | Tanaka et al. |
| 2008/0255416 A1 | 10/2008 | Gilboa |
| 2009/0153729 A1 | 6/2009 | Hiltunen et al. |
| 2012/0148225 A1 | 6/2012 | Chow et al. |
| 2013/0258182 A1 | 10/2013 | Lin et al. |
| 2014/0098208 A1 | 4/2014 | Makino |
| 2016/0112622 A1 | 4/2016 | Gressum |
| 2017/0310890 A1 | 10/2017 | Wan et al. |
| 2018/0070806 A1 | 3/2018 | Matsuo et al. |
| 2019/0089875 A1 | 3/2019 | Fan |
| 2019/0246884 A1 | 8/2019 | Lu |
| 2020/0274995 A1 | 8/2020 | Coleman |
| 2021/0037169 A1 | 2/2021 | Numasawa et al. |
| 2021/0242099 A1 | 8/2021 | Takeshita |
| 2021/0249393 A1 | 8/2021 | Wu et al. |

OTHER PUBLICATIONS

U.S. Appl. No. 17/504,105 Office Action dated Dec. 21, 2022, 13 pages.
U.S. Appl. No. 17/504,105 Final Office Action dated Jul. 27, 2023, 16 pages.

* cited by examiner

ENDOSCOPE TIP ASSEMBLY USING TRUNCATED TRAPEZOID CAVITY INTERPOSER TO ALLOW COPLANAR CAMERA AND LEDS IN SMALL-DIAMETER ENDOSCOPES

RELATED APPLICATIONS

The present document is a continuation-in-part of U.S. patent application Ser. No. 17/504,105 filed Oct. 18, 2021. The entire contents of the aforementioned patent application is incorporated herein by reference.

BACKGROUND

Endoscopes have become common in Medicine to inspect tissues or observe and direct surgery without having to make large incisions so the unaided eye can see those tissues, and similar devices are often used for inspection in tight places of mechanical devices to avoid requiring disassembly. Typically, a distal end of the endoscope is inserted into the tight places or into the body, and a physician or other user observes images displayed through a display apparatus near a proximal end of the endoscope.

Past endoscopes often had cameras with lenses that focused light onto an end of a coherent optical fiber bundle at the distal end of the endoscope, and directed light through an optical fiber from an external illuminator onto tissue or parts to be inspected located in front of the lenses; the optical fiber brought images from the distal end of the endoscope to display apparatus near the proximal end of the endoscope.

As electronic cameras have become smaller, there is an increasing trend towards placing light sources, such as light emitting diodes (LEDs) or laser diodes, and electronic cameras, at the distal end of the endoscope and transmitting signals from the electronic cameras to the display apparatus near the proximal end of the endoscope.

Chip-type electronic cameras have become common in cell phones and similar devices. They are formed at wafer level by bonding a wafer of image sensor integrated circuits to a spacer wafer, and bonding to the spacer wafer a wafer of lenses, such that a lens is positioned in front of and spaced at a focal length from, each image sensor. The composite wafer is then diced into individual cameras by sawing and the cameras are then surface mountable to a substrate.

If LEDs and chip-type electronic cameras are surface-mounted on a single flat substrate at the distal end of the endoscope, because LEDs are much thinner than chip-type electronic cameras the cameras may shade portions of a field of view ahead of the distal end of the endoscope.

SUMMARY

In an embodiment, a cavity interposer has a cavity, first bondpads adapted to couple to a chip-type camera cube disposed within a base of the cavity at a first level, the first bondpads coupled through feedthroughs to second bondpads at a base of the interposer at a second level; and third bondpads adapted to couple to a light-emitting diode (LED), the third bondpads at a third level. The third bondpads coupled to fourth bondpads at the base of the interposer at the second level; and the second and fourth bondpads couple to conductors of a cable with the first, second, and third level different. In embodiments, an endoscope optical includes the cavity interposer an LED, and a chip-type camera cube electrically bonded to the first bondpads; the LED is bonded to the third bondpads; and a top of the chip-type camera cube and a top of the LED are at a same level.

BRIEF DESCRIPTION OF THE FIGURES

In the figures, same reference numbers in a first and second figures indicate structures having essentially the same description and function as illustrated in the first and second figures.

DETAILED DESCRIPTION OF THE EMBODIMENTS

Figure 1A:
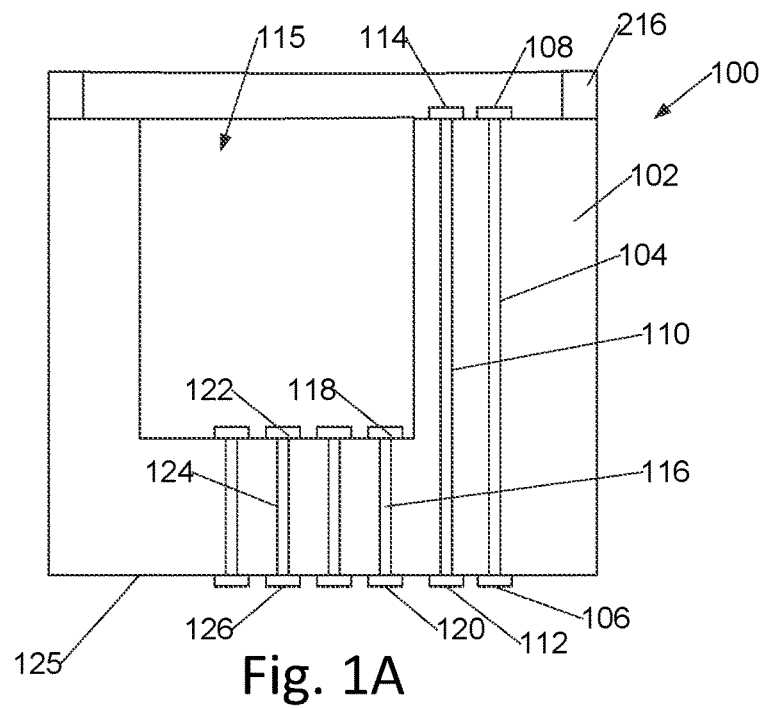
FIG. 1A is a schematic illustration of a cross section of a cavity interposer—a substrate allowing for surface-mounting a camera with lens at a same level as adjacent LEDs.
Figure 2:
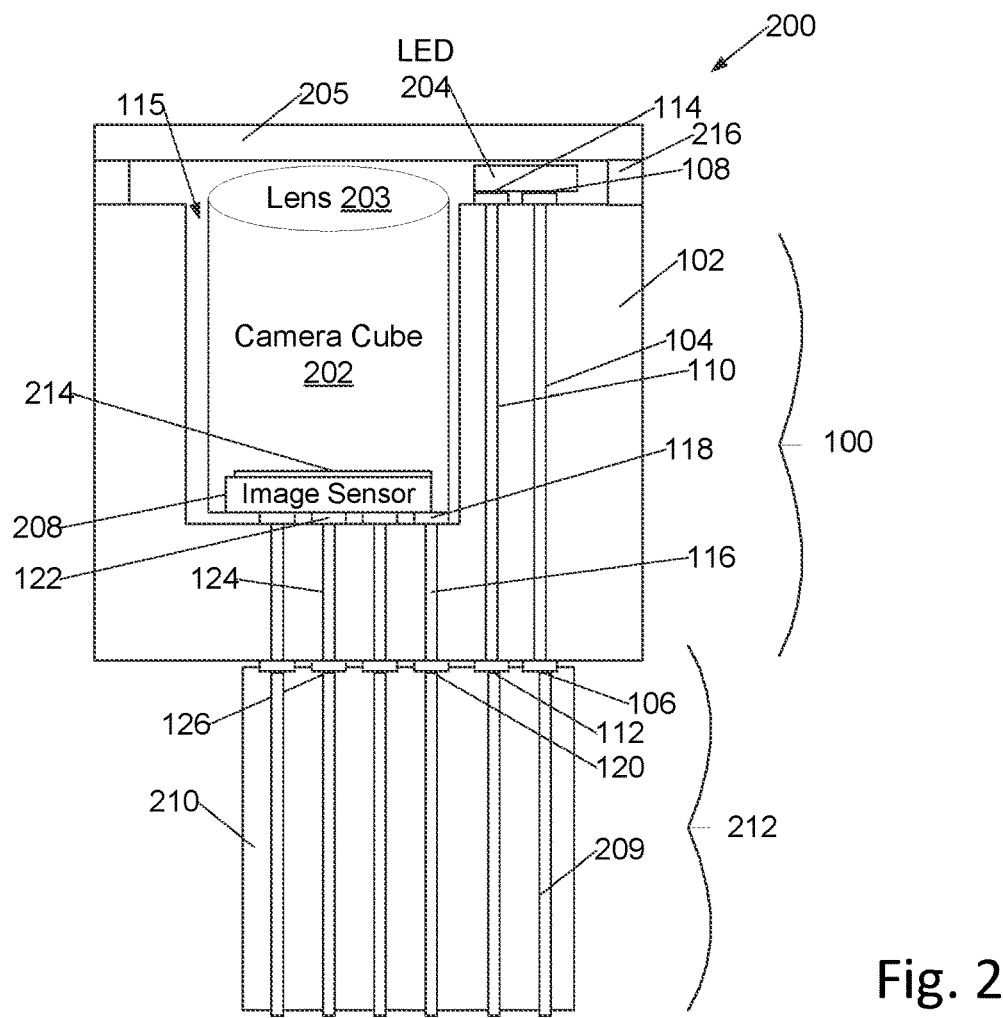
FIG. 2 is a schematic illustration of an optical endoscope head including the cavity interposer of FIGS. 1A, B.

A cavity interposer 100 (FIG. 1A) includes a substrate 102 having feedthrough conductors 104, 110 connecting bondpads 108, 114 adapted for ball-bond mounting of light emitting diodes to bondpads 108, 114 adapted to attaching to conductors of a connecting cable. Interposer 100 has a cavity 115 adapted to contain a chip-type "camera cube", having bondpads 118, 122 adapted for ball-bonding to mount a chip-type camera cube (as shown in FIG. 2). Bondpads 118, 122 are coupled through conductive feedthroughs 116, 124 to bondpads 120, 126 at a base 125 of the cavity interposer 100 adapted for attaching individually to conductors of the connecting cable. The cable may have as few as five conductors, although many embodiments, including those with fluorescent stimulus LEDs (see below), may have more than five conductors.

In an embodiment, the cavity interposer 100 is assembled into an endoscope optical head assembly 200 (FIG. 2) with camera cube 202 positioned in cavity 115 with bondpads of camera cube 202 bonded to bondpads 118, 122. Optical head assembly also includes at least one light-emitting diode (LED) 204 bonded to bondpads 108, 114 and configured to illuminate objects within a field of view that can be imaged by camera cube 202, in a particular embodiment, LED 204 is a white LED. Endoscope optical head assembly 200 also has a transparent protective window 205 sealed with waterproof material and positioned to protect the camera cube 202 and LED 204; to support the transparent protective window 205 above camera cube 202 and LED 204, the cavity interposer may in some embodiments have a rim 216 to support the transparent protective window 205. Camera cube 202 includes an imaging lens 203 and an image sensor 208, together with a spacer (not shown in FIG. 2) that provides sufficient space between imaging lens 203 and image sensor 208 to focus images of objects within the field of view onto the image sensor 208. Typically, image sensor 208 incorporates a color filter array 214 with a tiling pattern of color filters, such as a Bayer-pattern tiling pattern, the color filter array including red, green, and blue bandpass filters to provide full-color images. Camera cube 202 is configured, typically with solder bumps on its lower surface, for bonding to bondpads 118, 122 of cavity interposer 100, and in an embodiment is ball bonded to bondpads 118, 122 of cavity interposer 100. In an alternative embodiment, bondpads of camera cube 202 are electrically bonded to bondpads 118, 122 of cavity interposer 100 with electrically conductive, silver-containing, glue or with an anisotropic conductive film. In the endoscope optical head, bondpads 106, 112, 120, 126, of the lower surface of the cavity interposer 100 are attached to conductors 209 formed on a flexible substrate 210 to form a flexible endoscope cable 212. In an embodiment, a top of camera cube 202 is at the same level as a top of LED 204.

Figure 1B:
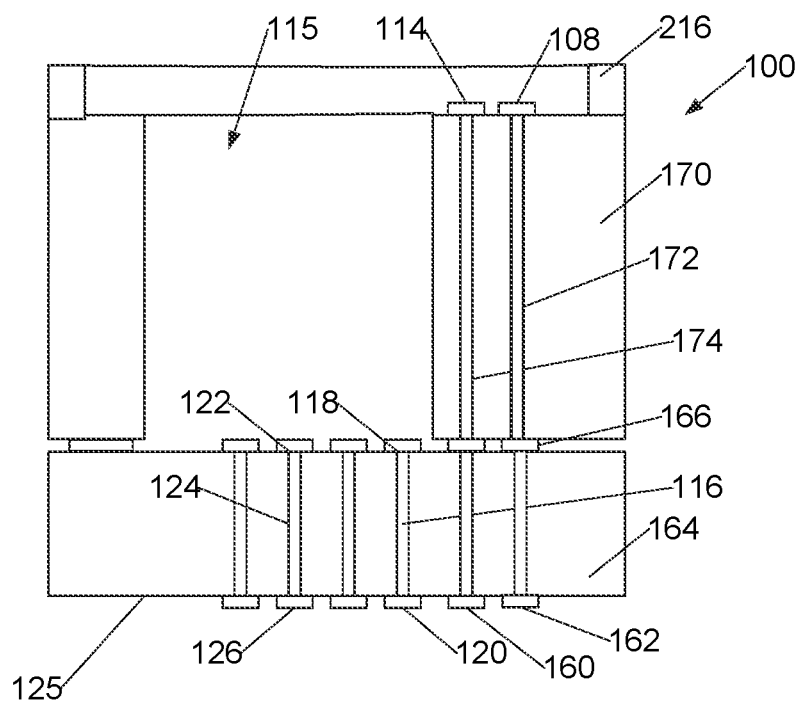
FIG. 1B is a schematic illustration of a cross section of a cavity interposer formed of two layered portions.

In a particular embodiment, the cavity interposer is assembled from two wafers of substrate material, a lower part 164 (FIG. 1B) is formed multiple lower cavity interposer portions with feedthroughs 116, 124, 160, 162 and appropriate bondpads 120, 112, 126, and an upper part 170 with multiple cavity interposer portions within which cavity 115 is formed. Upper part 170 is formed with feedthroughs 172, 174 that align with feedthroughs 160, 162 of the lower part 164 to form the long feedthroughs 104, 110 that reach to the level where LEDs will be bonded, and to bondpads 108, 114 used for LEDs, while feedthroughs 124 reach bondpads 122, 118, that are adapted for attaching the camera cube 202 (FIG. 2). The two wafers are then bonded together, such that the feedthroughs 160, 162 of the lower part are electrically connected to aligned feedthroughs 172, 174 of the upper part and the cavity 115 is in a correct place, then the wafers are diced to form cavity interposers. In an alternative embodiment, camera cubes 202 and LEDs 204 are bonded into cavity 115 and to bondpads of the cavity interposer before the wafers are diced to form optical head assemblies.

In embodiments having rim 216, the rim may be formed as a third wafer and bonded to the wafer having the upper part of the cavity interposer prior to dicing the wafers. In some of these embodiments, the transparent lid (not shown) is attached over the rim prior to dicing the wafers. In an alternative embodiment, instead of sealing a transparent lid over the camera cube and LEDs, a transparent plastic material is injected into the cavity formed by the rim and serves to cover and protect both the camera cube and the LEDs. Both the transparent lid and the transparent plastic material serve as protection for the camera cube, LEDs, and any bondwires present within the cavity formed by the rim.

In an embodiment, cavity interposer 100 is a multilayered ceramic structure with cavity 115 formed in one or more layers before the layers are fired together. In an alternative embodiment, cavity interposer 100 is formed of composite materials such as injection-molded plastic or printed-circuitry board material, in this alternative embodiment, holes for feedthroughs 116, 124, 104, 110 may be formed by laser drilling, and the cavity 115 may be formed by mechanical drilling; in an embodiment where cavity interposer is formed of printed-circuit board material, the cavity interposer may be formed of one or more layers of insulating material, two or three layers of conductive material, and one or more layers of insulating support material. Once formed, holes for feedthroughs in some embodiments are plated through to form feedthroughs 116, 124, 104, 110 and in other embodiments feedthroughs 116, 124, 104, 110 are formed by chemical vapor deposition (CVD) or evaporative metal deposition.

In an embodiment, flexible substrate 210 is formed of flexible printed circuit material, and conductors 209 are covered with an insulating material except where bonded at a distal end to bondpads of the cavity interposer and where bonded at a proximal end to additional circuitry.

In an alternative embodiment, cavity interposer 300 (FIG. 3) is formed such that bondpads 302 associated with the LEDs 304 are not directly under the LEDs (as shown in FIGS. 1 and 2), but are instead adjacent to and at a higher level than a shelf 306 such that an upper surface of LEDs 304 and an upper surface of bondpads 302 are coplanar. With this embodiment, instead of solder-ball bonding LEDs 304, LEDs 304 may be wirebonded to bondpads 302, coupled to bondpads 302 by an anisotropic conductive film 310, or coupled to bondpads 302 by a thin flexible printed circuit. In this embodiment, LED-associated feedthroughs 312 are longer than LED-associated feedthroughs 104 of the embodiment of FIGS. 1 and 2.

Figure 4:
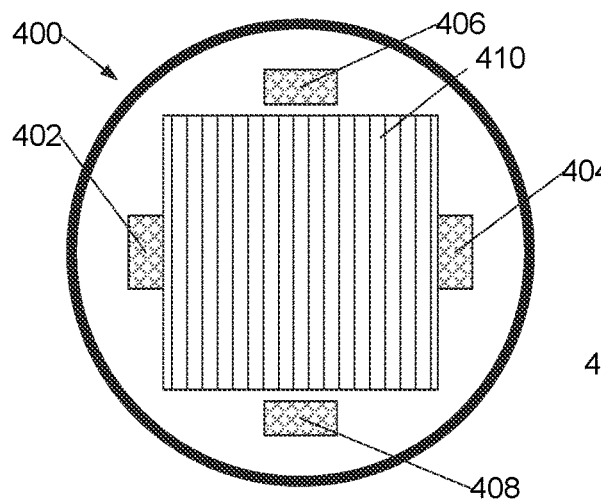
FIG. 4 is a top view of a round optical endoscope head showing mounted LEDs and camera cube.

In a round-interposer 400 (FIG. 4) embodiment there lies beneath window 205 a first LED 402, an optional second LED 404, an optional third LED 406, and an optional fourth LED 408, the LEDs flanking a camera cube 410. In a square-interposer 500 (FIG. 5) embodiment, there also lies beneath window 205 a first LED 402, an optional second LED 404, an optional third LED 406, and an optional fourth LED 408, the LEDs flanking a camera cube 410.

In alternative embodiments, there may be more than one LED, in some embodiments at least one white LED is provided for white-light color imaging and a separate fluorescent-imaging LED is provided and adapted to provide a fluorescent stimulus wavelength, fluorescent-imaging LED may have a filter to block light of wavelengths that pass through fluorescent-imaging tiles of color filter array 214. In embodiments having a fluorescent stimulus or excitation wavelength LED, there may be a fluorescence-stimulus wavelength-blocking filter incorporated into the tiling pattern of the color filter array 214 that is configured to pass light of a fluorescent emissions wavelength of a fluorophore of interest, and the color filter array 214 may be tiled with a color filter tiling patterns including more than the three, red, green, and blue, filters of a traditional Bayer-pattern filter. In particular embodiments, in addition to red, green, and blue filters in each tiling pattern there are color filters having a passband in the near-infrared, and one or more color filters having passbands associated with each of one or more fluorophores. For example, the embodiment of FIG. 5 may be assembled with two white-light LEDs 402, 404 disposed on opposite sides of camera cube 410, and two fluorescence stimulus wavelength LEDs 406, 408. In alternative embodiments, there may be fluorescence stimulus wavelength LEDs of several different wavelengths to allow detection of, and discrimination between, multiple fluorophores in tissue.

The endoscope optical head assembly 200 is used as a component of an endoscope or other device requiring imaging in tight spots such as borescope for performing optical inspections of cylinder bores of engines or interiors of barrels of guns. Medical uses of endoscopes using the optical head assembly include colonoscopes, hysteroscopes, laparoscopes, and sigmoidoscopes as well as laryngoscopes.

In particular embodiments, the entire endoscope optical head 800, 900, or 600, including interposer, has an outside diameter of less than one and a half millimeters and is particularly adapted for use in small-diameter endoscopes such as bronchoscopes, falloposcopes, and cystoscopes.

Figure 6:
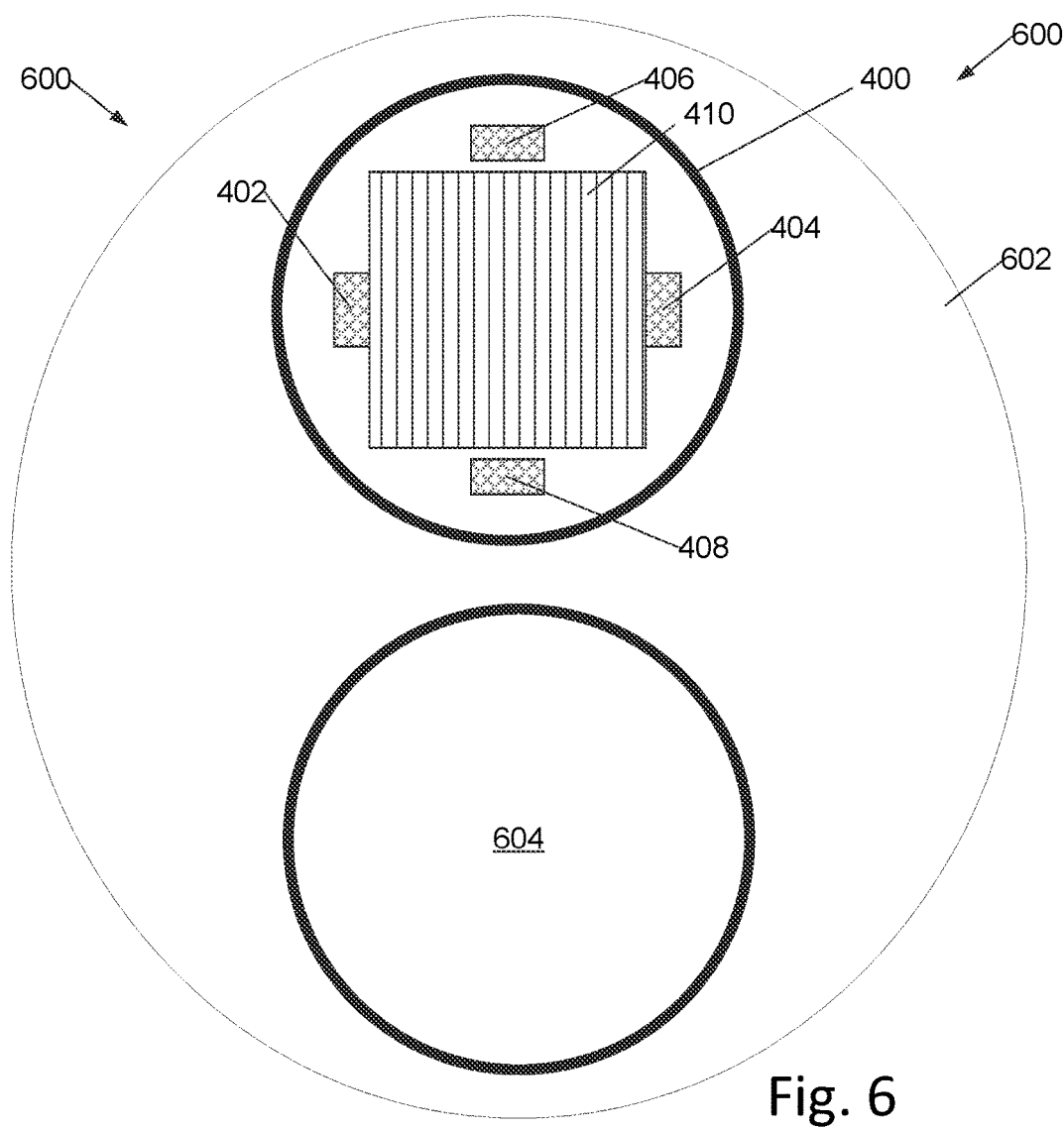
FIG. 6 is an end view of an endoscope incorporating the optical endoscope head of FIG. 4.
Figure 7:
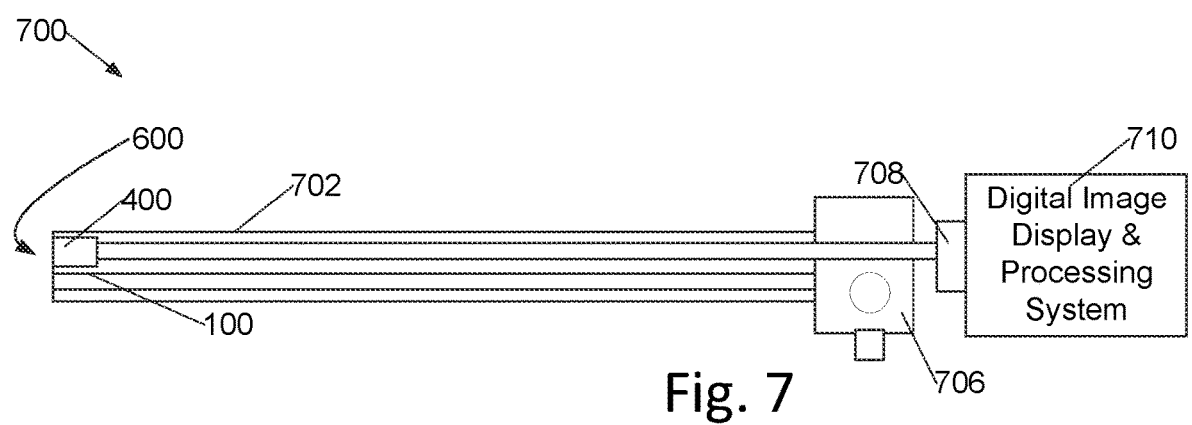
FIG. 7 is a schematic illustration of a cross section of an endoscope incorporating the optical endoscope head of FIG. 2 or FIG. 4.

In a typical endoscopic application, an endoscope end 600 (FIG. 6) includes an end of an endoscope body 602, the cavity interposer 400, attachment points for one or more steering wires (not shown), and an opening of a lumen 604 through endoscope body 602 through which operative tools such as but not limited to electrocauteries, wire loops, and cell samplers may reach a field of view in front of the endoscope optical head 600, 800, or 900. The endoscope end 600 forms an end of endoscope 700 with endoscope body 702, cavity interposer 400, 500, 802, or 902, operating handle 706 that may include controls for steering wires, and a connector 708 to an electronic digital image display & processing system 710 that displays images for guidance to a physician or other user.

Figure 3:
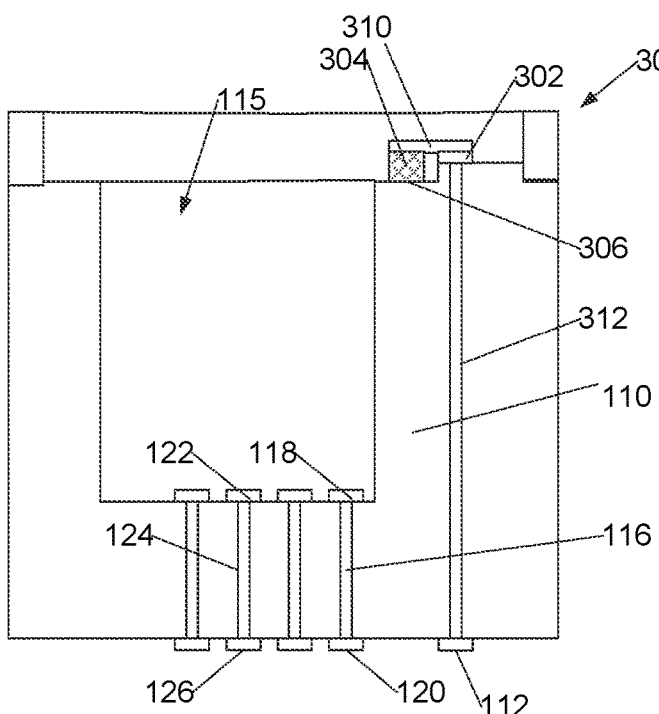
FIG. 3 is a schematic cross section illustration of an alternative embodiment of a cavity interposer showing an attached LED.

In embodiments, the endoscope optical head is formed by fabricating a wafer of cavity interposers, the cavity interposers individually shaped as describe with reference to FIG. 1 or FIG. 3, but not yet diced into individual cavity interposers. Individual diced chip-type cameras are then inserted into, and bonded to bondpads at a first level of, each cavity of the cavity interposers, and LEDs are also attached and bonded to bondpads of a third level of the cavity interposers. Each bondpad of first and third level of the interposers is coupled through feedthroughs to bondpads of the cavity interposers at a second level.

In embodiments lacking rim 216, a spacer wafer may be bonded to the wafer of cavity interposers. A wafer of protective windows is then bonded atop the cavity interposers or atop the spacer wafer. The cavity interposer is then diced, typically by sawing, and conductors of cables are attached to the second level bondpads of the cavity interposers.

Figure 5:
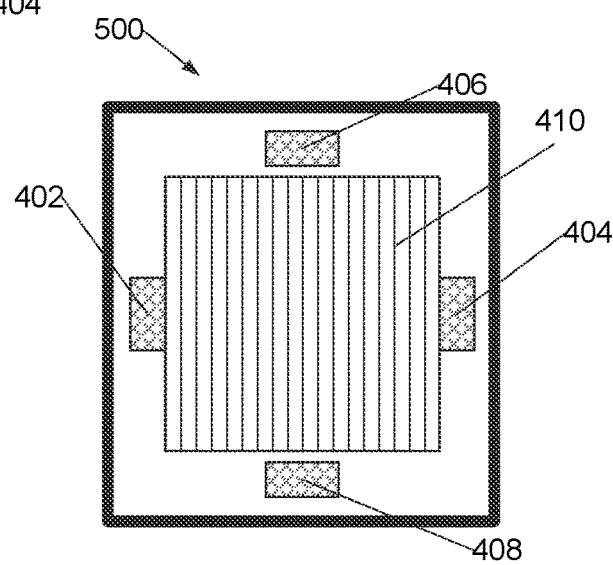
FIG. 5 is a top view of a rectangular optical endoscope head showing mounted LEDs and camera cube.
Figure 8:
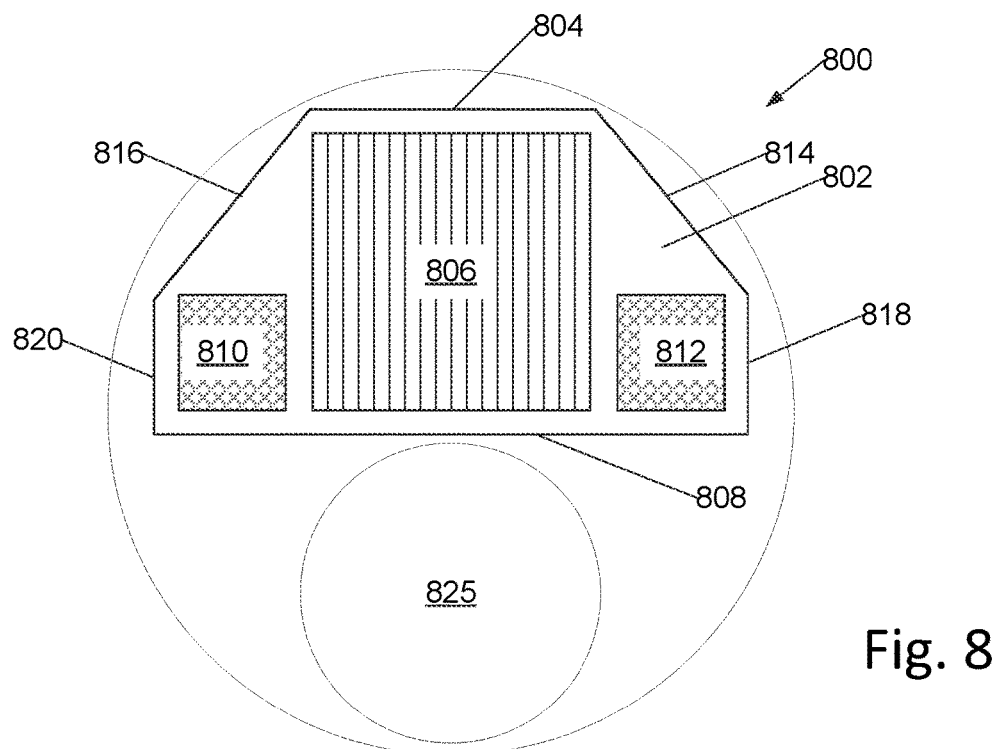
FIG. 8 is a schematic top plan view of a cavity interposer having truncated-trapezoidal shape configured for use in small-diameter endoscopes.

In some embodiments, particularly appropriate for use in small-diameter endoscope heads 800 (FIG. 8), the cavity interposer 802 has truncated isosceles trapezoidal shape. In these embodiments, a short parallel side 804 of the cavity is configured to be positioned against a curved interior side of endoscope head 800; short parallel side 804 is adjacent camera cube 806. Long parallel side 808 is configured to be positioned more centrally to endoscope head 800 and is adjacent to camera cube 806 and two LEDs 810, 812, one LED being positioned on each side of camera cube 806 and positioned nearer to long parallel side 808 than to short parallel side 804. Isosceles side 814, 816, extend downward from short parallel side 804 at a 45-degree angle towards, but do not meet, long parallel side 808, and terminate in a vertical truncation side 818, 820 after providing room for LEDs 810, 812. Use of the truncated isosceles trapezoidal shaped cavity interposer may provide more room for endoscope lumens 825 or other functional portions of endoscope head 800 than may be available with a square interposer as illustrated in FIG. 5.

Figure 9:
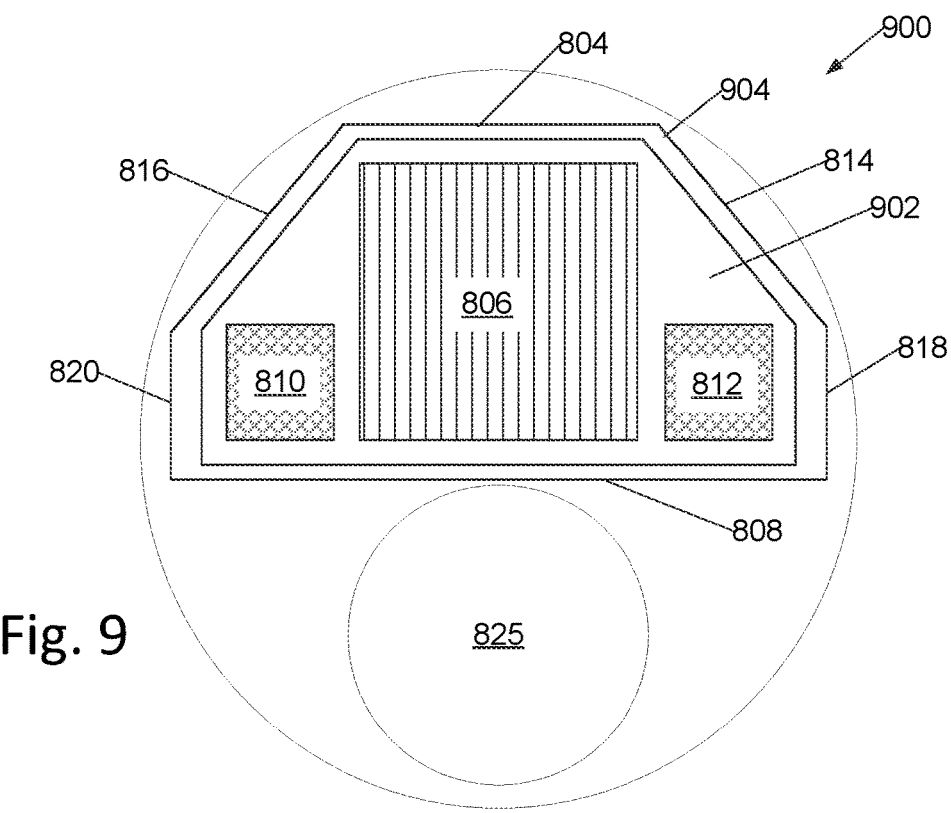
FIG. 9 is a schematic top plan view of the cavity interposer from FIG. 8 having a rim to which a lid may be sealed or which may be filled with a transparent plastic material.

In some embodiments of an endoscope head 900 (FIG. 9), the cavity interposer 902 has a rim 904 to which a lid (not shown) may be sealed or which may be filled with a transparent plastic material as heretofore described with reference to rim 216.

Combinations

The cavity interposer, camera cube, LEDs, and cable herein described may be configured in a number of ways. Among configurations anticipated by the inventors are:

A cavity interposer designated A has a body configured with a cavity, a plurality of first bondpads adapted to couple to bondpads of a chip-type camera cube (CCube), the first bondpads disposed within a base of the cavity at a first level, the first bondpads coupled through feedthroughs to second bondpads at a base of the cavity interposer at a second level; and a plurality of third bondpads adapted to couple to bondpads of an light-emitting diode (LED), the third bondpads disposed at a third level. The third bondpads coupled through feedthroughs to fourth bondpads at the base of the cavity interposer at the second level; and the second and fourth bondpads are adapted to couple to conductors of a cable with the first, second, and third level different.

An endoscope optical head designated AA includes the cavity interposer designated A, at least one LED, and a chip-type camera cube, where the chip-type camera cube is electrically bonded to the first bondpads; the LED is bonded to the third bondpads; and a top of the chip-type camera cube and a top of the LED are at a same level.

An endoscope optical head designated AB includes the endoscope optical head designated AA and has a cable comprising a plurality of electrical conductors, the plurality of electrical conductors bonded to bondpads of second or fourth bondpads.

An endoscope optical head designated AC includes the endoscope optical head designated AA or AB and has the LED is ball bonded to the third bondpads.

An endoscope optical head designated AD includes the endoscope optical head designated AA or AB and has the LED wire bonded to the third bondpads, and where the third bondpads are at a same level as the top of the LED An endoscope optical head designated AE includes the endoscope optical head designated AA, AB, AC, or AD wherein the camera cube has a tiling pattern including an infrared optical filter.

An endoscope optical head designated AF includes the endoscope optical head designated AA, AB, AC, AD, or AE wherein there are a plurality of LEDs, and at least one LED is a white LED and at least one LED is a fluorescent stimulus wavelength LED.

A cavity interposer designated B including the cavity interposer designated A with a truncated isosceles trapezoidal shape in top plan view.

An endoscope head designated BA including the cavity interposer designated B, a first white LED, a second fluorescent stimulus wavelength LED, and a chip-type camera cube ball-bonded to the first bondpads.

An endoscope head designated BB including the cavity interposer designated B, at least two LEDs, and a chip-type camera cube, where: the chip-type camera cube is ball-bonded to the first bondpads; the two LEDs are bonded to the third bondpads, the two LEDs being on opposite sides of the chip-type camera cube and closer to a long parallel side of the cavity interposer than to a short parallel side of the cavity interposer; and a top of the chip-type camera cube and a top of the LED are at a same level.

An endoscope head designated BC including the cavity interposer designated B, BA, or BB wherein the cavity interposer further comprises a rim and further includes protection for the camera cube selected from the group consisting of a transparent lid sealed to the rim and a transparent plastic material in a space formed by the rim of the cavity interposer.

An endoscope head designated BD including the cavity interposer designated B, wherein the truncated isosceles trapezoidal shape of the cavity interposer comprises two isosceles sides of the cavity interposer each extending at a 45 degree angle from the short parallel side of the cavity interposer and terminating in a short vertical side of the cavity interposer that extends to the long parallel side of the cavity interposer.

An endoscopic imaging system designated C includes an endoscope comprising a cavity interposer having a body configured with a cavity, the body comprising a plurality of first bondpads adapted to couple to bondpads of a chip-type camera cube (CCube), the first bondpads disposed within a base of the cavity at a first level, the first bondpads coupled through feedthroughs to second bondpads at a base of the cavity interposer at a second level; and a plurality of third bondpads adapted to couple to bondpads of an light-emitting diode (LED), the third bondpads disposed at a third level; the third bondpads coupled through feedthroughs to fourth bondpads at the base of the cavity interposer at the second level; the second and fourth bondpads adapted to couple to conductors of a cable; and the first, second, and third level are different; a chip-type camera cube disposed within the cavity and having bondpads electrically coupled to the cavity interposer; a light emitting diode mounted to the third bondpads; a cable having a first end coupled to the second and fourth bondpads and a second end coupled to a connector; and the connector is electrically connected to a digital image display and processing system.

A system designated CA including the system designated C wherein the endoscope further comprises a second LED coupled to bondpads of the cavity interposer, the second LED being adapted to provide light at a fluorescent stimulus wavelength, and the chip-type camera cube having a color filter array tiled with a pattern comprising a filter configured to block light of the fluorescent stimulus wavelength while passing light of a fluorescent emissions wavelength.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween. It is also anticipated that steps of methods may be performed in an order different from that illustrated and still be within the meaning of the claims that follow.

What is claimed is:

1. A cavity interposer having a body configured with a cavity, the body comprising:
   a plurality of first bondpads adapted to couple to bondpads of a chip-type camera cube (CCube), the first bondpads disposed within a base of the cavity at a first level, the first bondpads coupled through feedthroughs to second bondpads at a base of the cavity interposer at a second level; and
   a plurality of third bondpads adapted to couple to bondpads of an light-emitting diode (LED), the third bondpads disposed at a third level;
   the third bondpads coupled through feedthroughs to fourth bondpads at the base of the cavity interposer at the second level;
   the second and fourth bondpads adapted to couple to conductors of a cable; and the first, second, and third level are different.

2. An endoscope optical head comprising the cavity interposer of claim 1, at least one LED, and a chip-type camera cube, where:
   the chip-type camera cube is ball-bonded to the first bondpads;
   the LED is bonded to the third bondpads; and
   a top of the chip-type camera cube and a top of the LED are at a same level.

3. The endoscope optical head of claim 2, further comprising:
   a cable comprising a plurality of electrical conductors, the plurality of electrical conductors bonded to bondpads of second or fourth bondpads.

4. The endoscope optical head of claim 3, wherein the LED is ball bonded to the third bondpads.

5. The endoscope optical head of claim 4, wherein the camera cube has a tiling pattern including an infrared optical filter.

6. The endoscope optical head of claim 5, wherein there are a plurality of LEDs, and at least one LED is a white LED and at least one LED is a fluorescent stimulus wavelength LED.

7. The endoscope optical head of claim 3, wherein the LED is wire bonded to the third bondpads, and where the third bondpads are at a same level as the top of the LED.

8. The endoscope optical head of claim 7, wherein the chip-type camera cube has a tiling pattern including an infrared optical filter.

9. The endoscope optical head of claim 8, wherein there are a plurality of LEDs, and at least one LED is a white LED and at least one LED is a fluorescent stimulus wavelength LED.

10. The cavity interposer of claim 1 having a truncated isosceles trapezoidal shape in top plan view.

11. An endoscope head comprising cavity interposer of claim 10, a first white LED, a second fluorescent stimulus wavelength LED, and a chip-type camera cube ball-bonded to the first bondpads.

12. An endoscope optical head comprising the cavity interposer of claim 10, at least two LEDs, and a chip-type camera cube, where:
   the chip-type camera cube is ball-bonded to the first bondpads;
   the two LEDs are bonded to the third bondpads, the two LEDs being on opposite sides of the chip-type camera cube and closer to a long parallel side of the cavity interposer than to a short parallel side of the cavity interposer; and
   a top of the chip-type camera cube and a top of the LED are at a same level.

13. The endoscope optical head of claim 12, wherein the cavity interposer further comprises a rim and further comprising protection for the camera cube selected from the group consisting of a transparent lid sealed to the rim and a transparent plastic material in a space formed by the rim of the cavity interposer.

14. The endoscope optical head of claim 13, wherein the truncated isosceles trapezoidal shape of the cavity interposer comprises two isosceles sides of the cavity interposer each extending at a 45 degree angle from the short parallel side of the cavity interposer and terminating in a short vertical side of the cavity interposer that extends to the long parallel side of the cavity interposer.

15. An endoscopic imaging system includes an endoscope, comprising:
   a chip-type camera cube;
   a cavity interposer having a body configured with a cavity, the body comprising a plurality of first bondpads coupled to bondpads of a chip-type camera cube (CCube), the first bondpads disposed within a base of the cavity at a first level, the first bondpads coupled through feedthroughs to second bondpads at a base of the cavity interposer at a second level; and a plurality of third bondpads adapted to couple to bondpads of an light-emitting diode (LED), the third bondpads disposed at a third level; the third bondpads coupled through feedthroughs to fourth bondpads at the base of the cavity interposer at the second level; the second and fourth bondpads coupled to conductors of a cable; and the first, second, and third level are different;

a light emitting diode mounted to the third bondpads;

the cable having a second end coupled to a connector; and the connector electrically connected to a digital image display and processing system.

16. The system of claim 15, wherein the endoscope further comprises a second LED coupled to bondpads of the cavity interposer, the second LED being adapted to provide light at a fluorescent stimulus wavelength, and the chip-type camera cube having a color filter array tiled with a pattern comprising a filter configured to block light of the fluorescent stimulus wavelength while passing light of a fluorescent emissions wavelength.

* * * * *